United States Patent

Rygas et al.

[11] Patent Number: 5,902,914
[45] Date of Patent: May 11, 1999

[54] PROCESS FOR THE PREPARATION OF HALOGENATED ALKANES

[75] Inventors: Tadeusz Piotr Rygas, Niagara, Canada; Hsueh Sung Tung, Getzville; Addison Miles Smith, Amherst, both of N.Y.

[73] Assignee: AlliedSignal Inc., Morristown, N.J.

[21] Appl. No.: 08/514,545

[22] Filed: Aug. 14, 1995

[51] Int. Cl.$^6$ ............................. C07C 17/30; C07C 21/18
[52] U.S. Cl. ............................................ 570/257; 570/172
[58] Field of Search ..................................... 570/172, 257

[56] References Cited

U.S. PATENT DOCUMENTS 3,862,978   1/1975   Decker et al. .

OTHER PUBLICATIONS

Kotora et al. "Selective Addition of Polyhalogenated Compounds to Chlorosubstituted Ethenes Catalyzed by a Copper Complex," *React. Kinet. Catal. Lett.* vol. 44, No. 2, 415–419 (1991).

*Bulletin of the Academy of Sciences of the USSR Division of Chem ICAL Science,* vol. 29, No. 6, 1980.

Zhiryukina et al. Synthesis of Polychloroalkanes with Several Different Chlorine–Containing Groups, Translated from Izvestiya Akademii Nauk SSSR, Seriya Khimcheskaya, No. 1, 152–157 (1983).

Kotora et al. "Addition of Tetrachloromethane to Halogenated Ethenes Catalyzed by Transition Metal Complexes," *Journal of Molecular Catalysis,* 77(1992) 51–60.

*Primary Examiner*—Alan Siegel
*Attorney, Agent, or Firm*—Jay P. Friedenson; Marie Collazo

[57] ABSTRACT

A process for the preparation of halogenated alkanes is provided. In particular, a process is provided for the highly selective preparation of haloalkanes, including 1,1,1,3,3-pentachloropropane, pentachlorobutane, and hepatchlorohexane, in good yield.

22 Claims, No Drawings

PROCESS FOR THE PREPARATION OF HALOGENATED ALKANES

FIELD OF THE INVENTION

The present invention relates to a process for the preparation of halogenated alkanes. In particular, the present invention provides a process for the highly selective preparation of haloalkanes in good yield.

BACKGROUND OF THE INVENTION

The production of haloalkanes by the addition of olefins to starting material haloalkanes is well known in the art. Further, it is known that the product's carbon chain length increases by at least one carbon atom compared to the starting material, which drastically increases the product's boiling point making recovery of the product difficult and diminishing product yield.

Several addition reactions for producing synthetically useful haloalkanes, such as 1,1,1,3,3-pentachloropropane ("HCC-240"), are described in the prior art. For example, Kotora et al. "Addition of Tetrachloromethane to Halogenated Ethenes Catalyzed by Transition Metal Complexes", 77 *J. Molec. Catal.* 51–60 (1992) disclose the preparation of HCC-240 from carbon tetrachloride and vinyl chloride using both cuprous chloride and Cu[(CH$_3$–CN)$_4$]ClO$_4$ complexes with an n-butylamine cocatalyst. Catalyst and cocatalyst removal is achieved by water wash which destroys the catalyst. Additionally, the use of perchlorates in the process poses handling problems because perchlorates are extremely explosive.

Kotora et al., "Selective Addition of Polyhalogenated Compounds to Chlorosubstituted Ethenes Catalyzed by a Copper Complex", 44 *React. Kinet. Catal. Lett.* 415–19 (1991) disclose the preparation of HCC-240 from carbon tetrachloride and vinyl chloride using a cuprous chloride complex catalyst with 2-propylamine as a cocatalyst. The reported HCC-240 yield, however, is only 71%. Zhiryukina et al. "Synthesis of Polychloroalkanes With Several Different Chlorine-Containing Groups", 1 *Izv. Akad. Nauk SSR, Ser. Khim.* 152–57 (1983) disclose a process for preparing HCC-240 from carbon tetrachloride and vinyl chloride using an Fe(CO)$_5$-ethanol catalyst, which process reportedly yields 25% HFC-240. Both of these disclosed processes are disadvantageous in that they have a low selectivity for HFC-240. The Zhiryukina et al. process is further disadvantageous because it uses a highly toxic catalyst.

None of the prior art processes provides for haloalkane production in high yield and for the recycle of unreacted materials. Thus, a need exists for an efficient and economical process for the preparation of haloalkanes in high yield.

DESCRIPTION OF THE INVENTION AND PREFERRED EMBODIMENTS

The present invention provides a highly selective process for the production of halogenated alkanes in good yield in which process unreacted materials may be recycled. More specifically, the invention provides a process for producing halogenated alkanes which halogenated alkanes include, without limitation, prior art haloalkanes such as HCC-240 as well as haloalkanes not seen in the prior art such as pentachlorobutane ("HCC-360") and heptachlorohexane ("HCC-580"). HCC-240, 360, and 580 may be used as intermediates for the production of 1,1,1,3,3-pentafluoropropane ("HFC-245fa"), pentafluorobutane ("HFC-365"), and heptafluorohexane ("HFC-587"), respectively, which end-products are refrigerants, insulating gases, aerosol carriers, and solvents.

In general, the process of this invention uses a catalyst with an organic ligand cocatalyst, flash distillation of organic feeds, catalyst filtration and recycle, and vacuum distillation, optionally in the presence of a metal chelating compound, to produce and recover product in high yield. The process may be carried out in either a batchwise or a continuous system. The production system may be closed to provide complete recycle of the unreacted feed material haloalkane and haloalkene.

In the first step (A) of the process of the present invention, the feed material, a haloalkane and a haloalkene, are reacted in the presence of a catalyst and cocatalyst. The specific haloalkane and haloalkene used as feed material, as well as the catalyst, cocatalyst, and reaction conditions used will depend on the desired product. Suitable feed material is commercially available. Haloalkanes useful in the process of the present invention are of the formula $C_nH_mX_p$ wherein n is an integer from 1 to 200, preferably from 1 to 20, most preferably from 1 to 4, X is a halogen such as fluorine, chlorine, bromine, iodine, or mixtures thereof, and m and p are each independently 0 to 2n+2 provided that m+p=2n+2. Exemplary haloalkanes include, without limitation, carbon tetrachloride, 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane. Useful haloalkene feed material is of the formula $C_nH_yX_z$ wherein n is an integer from 2 to 200, preferably from 2 to 20 and most preferably from 2 to 4, X is a halogen such as fluorine, chlorine, bromine, iodine, or mixtures thereof, and y and z are each independently 0 to 2n provided that y+z=2n. Exemplary haloalkenes include, without limitation, vinyl chloride, 1,1 dichloroethene, trichloroethene, tetrachloroethene, chlorofluoroethene, 1,2dichloroethene, 1,1-dichloro-difluoroethene, 1-chloro-1-propene, and 1-chloro-1-butene. For the production of HCC-240, the preferred feed materials are carbon tetrachloride, available from Vulcan Chemicals, Birmingham, Ala. and vinyl chloride, available from PPG Industries, Pittsburgh, Pa. For HCC-360 production, 1,1,1-trichloroethane and 1,1-dichloroethene, both available from PPG Industries, are preferred. For HCC-580 production, pentachlorobutane and 1,1dichloroethene are preferred.

Generally, the mole ratio of haloalkane to haloalkene is from about 0.02:1 to about 50:1. Preferably, the ratio is from about 1.2:1 to about 4.0:1 and more preferably from about 1.5:1 to about 2.5:1 haloalkane to haloalkene.

The catalysts useful in the present invention include metal ions. Suitable catalysts include cuprous salts, organometallic cuprous compounds, iron powder, and iron chloride. Exemplary cuprous salts and organometallic cuprous compounds include, without limitation, cuprous chloride, cuprous bromide, cuprous cyanide, cuprous sulfate, and cuprous phenyl. The iron powder used in this invention is a fine powder of pure metallic iron, preferably with a particle size smaller than 325 mesh. Preferably, cuprous chloride or iron powder is used.

The cocatalyst of the present invention is an organic ligand capable of forming a complex with the catalyst used and bringing the catalyst into solution. Suitable ligands include organic amines, such as, without limitation, tert-butylamine, n-butylamine, sec-butylamine, 2-propylamine, benzylamine, tri-n-butylamine, and pyridine. The preferred organic amine is tert-butylamine. Alternatively, the cocatalyst may be a nitrile including, without limitation, acetonitrile, propionitrile, n-butyronitrile, benzonitrile, and phenylacetonitrile. The preferred nitrile is acetonitrile. As yet another alternative, the cocatalyst may be an amide including, without limitation, hexamethylphosphoramide and dimethylformamide. Hexamethylphosphoramide is the preferred amide.

The catalysts and cocatalysts useful in the present invention are commercially available. Preferably, the catalyst-cocatalyst system is cuprous chloride-tert-butylamine or iron powder-hexamethylphosphoramide. Most preferably, iron powder-hexamethylphosphoramide is used.

The catalyst and cocatalyst are used in amounts sufficient to catalyze the reaction of the feed material. Generally, the amount used is a mole ratio of catalyst to cocatalyst from about 0.01:1 to about 50:1, preferably from about 0.1:1 to about 3:1. The mole ratio of copper to t-butylamine is about 0.05:1 to about 2.0:1, preferably about 0.02:1 to 1.0:1, and more preferably about 0.1:1 to about 0.7:1. The mole ratio of iron powder to hexamethylphosphoramide may be about 0.05:1 to about 10.0:1, preferably about 1.0:1 to about 3.0:1, and more preferably about 1.5:1 to about 2.5:1. The preferred concentration of the catalyst in the reaction mixture is from about 0.01 to about 10 weight percent, preferably from about 1 to about 5 weight percent, and more preferably from about 1.5 to about 2.5 weight percent.

The catalyst may be added to the reactor containing the haloalkane, haloalkene, and cocatalyst. Alternatively, the haloalkane and haloalkene may be added to a reactor containing the catalyst and cocatalyst. As yet another alternative, and preferably, the catalyst, cocatalyst and haloalkane are mixed first, the mixture degassed by quick partial evacuation of the vapors, with or without cooling of the mixture, and the haloalkene is added to the mixture.

The reactor is heated to a temperature of from about 40° C. to about 180° C., preferably from about 85° C. to about 110° C., with agitation and under the vapor pressure of the reagents. The reaction is carried out until a conversion higher than 95% is achieved, generally for a period of from about 6 hours to about 24 hours, preferably from about 6 hours to about 12 hours.

After an initial period of high reaction rates, the reactor pressure may fall. At this point, optionally, the temperature may be increased an additional 10° to 60° to improve conversion.

In the second step (B) of the process, the product stream from step (A) is flash-distilled to remove unreacted haloalkane and haloalkene feed materials and cocatalyst. The distillation may be performed in one or more distillation columns which are well known in the art. Preferably, the flash distillation is conducted in two steps: first, flash distillation is conducted under atmospheric pressure at about 85° C. followed by vacuum flash distillation to remove unreacted haloalkane, haloalkene, and cocatalyst. The vacuum flash distillation should be carried out until the pressure falls to 50 mm Hg at 80° C., The distilled, unreacted haloalkane, haloalkene, and cocatalyst may be recycled back to the reactor.

In the third step (C), the "bottoms" stream, containing crude product and catalyst, from the flash distillation step (B) are filtered by any commonly known filter, preferably using vacuum or an inert gas pressure, such as nitrogen, to push the liquid through the filter. The catalyst may be recycled back to the reactor.

The fourth step (D) of the process of the present invention, provides for the purification of the crude product by distillation. Fractional vacuum distillation is carried out at about 5 to about 50 mm Hg and a temperature of about 89° C. to about 110° C. to recover the product. It has been discovered that, when step (D) is carried out in the presence of a trialkyl phosphate such as tributyl phosphate or other metal chelating compound, the distillation yield of purified product is significantly improved. Although not seeking to be bound by any particular theory, it is believed that the tributyl phosphate acts to prevent the decomposition of the product haloalkane. Thus, in a preferred embodiment, step (D) includes the addition of an amount of a metal chelating compound sufficient to improve the haloalkane product yield. Preferably, 5 weight percent of tributyl phosphate is used.

The process of the present invention and its use will be clarified further by a consideration of the following examples.

EXAMPLES

Example 1

1.56 g vinyl chloride and 64.25 g $CCl_4$ were added to an evacuated 100 ml pressure bottle containing 0.59 g iron powder and 1.0 g hexamethylphosphoramide. The bottle was immersed in an ultrathermostatic bath and equipped with a magnetic stirring bar and pressure gauge. The agitation was turned on and the bath warmed quickly to 100° C. The reaction was interrupted after six hours by quickly cooling the bath. The crude product, 63.63 g, was analyzed by GC and indicated formation of 1.12 g HCC-240. Selectivity was 100% based on vinyl chloride.

Example 2

0.52 g CuCl was added gradually to a mixture of 9.94 g vinylidene chloride, 50.20 g 1,1,1-trichloroethane, and 1.0 g t-butylamine in a 100 ml pressure bottle. The pressure bottle was immersed in an ultrathermostatic bath and equipped with a magnetic stirring bar and pressure gauge. The agitation was turned on and the bath quickly warned to 95° C. The reaction was interrupted after 6 hours by quick cooling of the bath. The crude product, 56.16 g, was analyzed using gas chromatography and an FID detector. Analysis of the crude product indicated formation of 0.82 g HCC-360. Selectivities were 82% based on vinylidene chloride and 90% based on 1,1,1-trichloroethane. Selectivity toward HCC-580 was 18.05% based on vinylidene chloride.

Example 2a 56.1 g of the crude reaction mixture is prepared as in Example 2 and is fractionally distilled at about 71° C., initially at atmospheric pressure and subsequently under reduced pressure, down to 20 mm Hg to recover the starting materials. Solid catalyst is precipitated from the distillation flask and is filtered off The filtrate, 9.48 g is fractionally distilled using a fractional distillation high vacuum column. 8.2 g pentachlorobutane is separated at 10 mm Hg and 71° C. Two isomers, 1,2,2,3,3-pentachlorobutane and 1,1,1,3,3-pentachlorobutane are seen.

Example 2b

Vacuum distillation as in Example 2a is continued with a two-stage oil vacuum pump. The material remaining in the distillation flask is distilled at 0.2 mm Hg and 84° C. 1.28 g pure heptachlorohexane is distilled. Four isomers, 1,2,2,4, 4,5,5-heptachlorohexane, 1,1,1,3,3,5,5-heptachlorohexane, 1,2,2,3,3,5,5-heptachlorohexane and 1,1,1,4,4,5,5-heptachlorohexane are seen.

Example 3

0.20 g CuCl was added gradually to a mixture of 1.81 g vinyl chloride and 65.47 g $CCl_4$ containing 0.50 g t-butylamine in a 100 ml pressure bottle. The bottle was immersed in an ultrathermostatic bath and equipped with a magnetic stirring bar and pressure gauge. The agitation was turned on and the bath quickly warned to 100° C. The reaction was interrupted after six hours by quickly cooling the bath. The crude product, 63.68 g, was analyzed by GC and indicated formation of 0.86 g HCC-240. Selectivity was 97.7% based on vinyl chloride.

Comparative Example 3

0.20 g CuCl was added gradually to a mixture of 4.52 g vinyl chloride and 61.55 g $CCl_4$ containing 1.08 g n-butylamine in a 100 ml pressure bottle. The bottle was immersed, equipped, agitated, warmed, reacted, and cooled as for Example 3. The crude product, 57.20 g, was analyzed using GC Analysis and indicated formation of 14.79 g HCC-240. Selectivity was 91.6% based on vinyl chloride.

The foregoing examples demonstrate that the use of t-butyl amine cocatalyst resulted in a higher selectivity than n-butylamine cocatalyst. Further, t-butyl amine boils at a lower temperature than n-butyl amine making it easier to recover by flash distillation so that it may be recycled.

Example 4

Flash distillation to recover unreacted material and cocatalyst was demonstrated using a synthetic mixture. Crude HCC-240 reaction product was simulated by mixing 1524 g crude HCC-240, 1481 g $CCl_4$, 28.05 g t-butylamine, and 14.24 g CuCl. $CCl_4$ and t-butylainine were recovered using flash distillation carried out in a 2 in. diameter, 2 ft long, column, initially under atmospheric pressure. When output of the distillation stopped, the pressure was gradually reduced to 55 mm Hg to ensure a continuous and steady distillation output. Almost all of the t-butylamine and $CCl_4$ was recovered from flash distillation. Solid catalyst, $CuCl/CuCl_2$, was precipitated out of the solution in the distillation flask.

Example 5

The solid-containing solution remaining in the distillation flask of Example 4 was removed to a Buchner funnel and filtered with No. 1 Whatman filter paper. The filtration was conducted using 60 mm Hg vacuum in an open system. The mother liquor consisted mainly of HCC-240. ICAP analysis indicated that it contained only 168 ppm copper catalyst.

Example 6

684.0 g of the filtered crude HCC-240 of Example 5 was charged to a 1000 ml round bottom flask in a vacuum distillation apparatus. 10.2 g tri(n-butylphosphate) was added. The charged material was flash distilled under 50 mm Hg vacuum at 89–90° C. The distillation was interrupted when the reboiler flask was almost empty and no more droplets of distillate were observed. The residual material contained 2.7 g HCC-240, a loss of 0.4% of the starting material and was brown in color without the presence of tars. The distillate weighed 668.6 g, 97.74% of the starting weight. Weight accountability of the distillation was 98.14%.

Comparative Example 6

721.1 g of the filtered crude HCC-240 of Example 5 was charged to a 1000 ml round bottom flask in a vacuum distillation apparatus. No tri(n-butylphosphate) was added. The material was distilled under 50 mm Hg vacuum at 89–90° C. The distillation was interrupted when beginning decomposition of the reboiler material was observed. The residual material in the reboiler flask became tarry and the distilled material dropping from the condenser turned brown. The reboiler was quickly cooled and the residual material weighed. The residue was tarry and difficult to remove from the flask. The weight of HCC-240 lost as reboiler residue was 55.5 g, 7.7% of the starting weight. The distillate weighed 642.1 g, 89.04% of the starting weight. Weight accountability of the distillation was 96.74%.

Examples 6 and Comparative Example 6 illustrate that the use of a metal chelating compound provides improved distillation yields and prevents the decomposition of product and tar formation.

Other embodiments of this invention will be apparent from a consideration of this specification or the practice of the invention disclosed herein. It is intended that the specification and examples be considered as exemplary only with the true scope and spirit of the invention being indicated in the following claims.

What is claimed is:

1. A process for producing a haloalkane, comprising the steps of:
   (A) reacting a feed material comprising a haloalkane and a haloakene in the presence of a catalyst and a cocatalyst under conditions suitable to produce a haloalkane product stream;
   (B) flash-distilling the haloalkane product stream of step (A) to produce a first stream comprising unreacted feed material and the cocatalyst and a second stream comprising a haloalkane product and the catalyst;
   (C) filtering the second stream of step (B) to remove the catalyst from the haloalkane product; and
   (D) distilling the baloalkane product in the presence of a metal chelating compound present in an amount sufficient to improve the haloalkane product yield.

2. The process of claim 1 wherein the catalyst is a cuprous salt and the cocatalyst is an organic ligand.

3. The process of claim 2 wherein the cuprous salt is cuprous chloride and the organic ligand is an organic amine.

4. The process of claim 3 wherein the organic amine is tert-butylamine.

5. The process of claim 1 wherein the catalyst is iron powder and the cocatalyst is an organic ligand.

6. The process of claim 5 wherein the organic ligand is an amide.

7. The process of claim 6 wherein the amide is hexamethylphosphoramide.

8. The process of claims 2 or 6 wherein the metal chelating compound is tributyl phosphate.

9. The process of claim 1 wherein the haloalkane is carbon tetrachloride and the haloalkene is vinyl chloride.

10. The process of claim 1 wherein the haloalkane is 1,1,1-trichloroethane and the haloalkene is 1,1,-dichloroethene.

11. The process of claim 1 wherein the haloalkane is pentachlorobutane and the haloalkene is 1,1,-dichloroethene.

12. A process for producing a haloalkane, comprising the steps of:
   (A) reacting a feed material comprising a haloalkane and a haloalkene in the presence of a catalyst and a cocalalyst under conditions suitable to produce a haloalkane product stream;

(B) flash-distilling the haloalkane product stream of step (A) to produce a first stream comprising unreacted feed material and the cocatalyst and a second stream comprising a haloalkane product and the catalyst;

(C) recycling the first stream of step (B) to step (A);

(D) filtering the second stream of step (B) to remove the catalyst from the haloalkane product;

(E) recycling the catalyst removed in step (D) to step (A); and (F) distilling the haloalkane product in the presence of a metal chelating compound present in an amount sufficient to improve the haloalkane product yield.

13. The process of claim 2 wherein the catalyst is a cuprous salt and the cocatalyst is an organic ligand.

14. The process of claim 13 wherein the cuprous salt is cuprous chloride and the organic ligand is an organic amine.

15. The process of claim 14 wherein the organic amine is tert-butylamine.

16. The process of claim 12 wherein the catalyst is iron powder and the cocatalyst is an organic ligand.

17. The process of claim 16 wherein the organic ligand is an amide.

18. The process of claim 17 wherein the amide is hexamethylphosphoramide.

19. The process of claims 14 or 17 wherein the metal chelating compound is tributyl phosphate.

20. The process of claim 12 wherein the haloalkane is carbon tetrachloride and the haloalkene is vinyl chloride.

21. The process of claim 12 wherein the haloalkane is 1,1,1-trichloroethane and the haloalkene is 1,1-dichloroethene.

22. The process of claim 12 wherein the haloalkane is pentachlorobutane and the haloalkene is 1,1,-dichloroethene.

* * * * *